United States Patent
Schorr et al.

(12) 
(10) Patent No.: US 6,465,438 B1
(45) Date of Patent: Oct. 15, 2002

(54) NUCLEIC ACID VACCINATION FOR PARVOVIRAL INFECTIONS

(75) Inventors: Joachim Schorr, Hilden (DE); Henry J. Baker; Bruce F. Smith, both of Auburn, AL (US)

(73) Assignee: Metin Colpan, Essen (DE)

( * ) Notice: Subject to any disclaimer, the term of this patent is extended or adjusted under 35 U.S.C. 154(b) by 0 days.

(21) Appl. No.: 09/171,425

(22) PCT Filed: Apr. 18, 1997

(86) PCT No.: PCT/EP97/01943

§ 371 (c)(1),
(2), (4) Date: Oct. 19, 1998

(87) PCT Pub. No.: WO97/40163

PCT Pub. Date: Oct. 30, 1997

(30) Foreign Application Priority Data

Apr. 19, 1996 (EP) ............................................. 96106217

(51) Int. Cl.[7] ........................ A61K 48/00; A61K 35/00; C12N 15/63
(52) U.S. Cl. ...................... 514/44; 424/93.1; 435/320.1
(58) Field of Search .......................... 514/44; 536/23.1; 435/235.1

(56) References Cited

U.S. PATENT DOCUMENTS

| 5,498,413 A | * | 3/1996 | Casal Alvarez et al. | . 424/233.1 |
| 5,863,541 A | * | 1/1999 | Samulski et al. | ......... 424/192.1 |
| 5,882,652 A | * | 3/1999 | Valdes et al. | ............ 424/221.1 |

FOREIGN PATENT DOCUMENTS

EP     0 647 655 A1     12/1995

OTHER PUBLICATIONS

Chattergoon et al. Genetic Immunization: A New Era in Vaccines and Immune Therapeutics. FASEB, vol. 11, pp. 753–763, Aug. 1997.*

Zinkernagel, R. M. Immunity to Viruses. Fundamental Immunology, 3rd Edition, Paul, W., ed., Chapter 34, pp. 1211–1250, 1993.*

McDonnell et al. Molecular Medicine DNA Vaccines. The New England Journal of Medicine, vol. 334, pp. 42–45, Jan. 4, 1996.*

Yoshimoto et al. A Second Neutralizing Epitope of B19 Parvovirus Implicates the Spike Region in the Immune Respones. Journal of Virology, vol. 65, pp. 7056–7060, Dec. 1991.*

Casal et al. Peptide vaccine against canine parvovirus: identification of two neutralization subsites in the terminus of VP2 and optimization of the amino acid sequence Nov. 1995 p. 7274–7277.*

Langeveld et al. First peptide vaccine providing protection against viral infection in the target animal: studies of canine parvovirus in dogs Jul. 1994,p. 4506–4513.*

H.C.J. Ertl et al., "Genetic Immunization", Jan. 1, 1996, Viral Immunology, 9:1, at 1–9.

J.P.M. Langeveld et al., "Effective induction of neutralizing antibodies with the amino terminus of vp2 of canine parvovirus as a synthetic peptide", 1994, Guildford GB, 12:15 at 1473–1480.

Lopez de Turiso, et al., "Fine mapping of canine parvovirus B cell epitopes", J. General Virologyu (1991) 72:2445–2456.

* cited by examiner

Primary Examiner—Michael C. Wilson
(74) Attorney, Agent, or Firm—Fish & Richardson P.C.

(57) ABSTRACT

The general field of the invention is a method for nucleic acid vaccination for animals to protect them from parvoviral infection. This invention is more particularly related to the preparation and use of parvoviral DNA and its administration to dogs, cats and mink so as to induce an immune response that can protect these animals from disease caused by virulante parvovirus. Nucleic acid immunogens are designed to include the antigenic portions of the parvoviral genome which are incorporated into bacterial plasmids. These plasmids produce the desired parvoviral gene product when introduced into host cells by transfection. Host cells transfected with the parvoviral immunogen expressing plasmids produce a stream ot antigenic proteins to which the host immune system will mount a protective immune response.

18 Claims, No Drawings

SEQUENCE LISTING

```
<160> NUMBER OF SEQ ID NOS: 14

<210> SEQ ID NO 1
<211> LENGTH: 42
<212> TYPE: DNA
<213> ORGANISM: Artificial Sequence
<220> FEATURE:
<223> OTHER INFORMATION: Synthetically generated oligonucleotides
<220> FEATURE:
<221> NAME/KEY: misc_feature
<222> LOCATION: (1)...(42)
<223> OTHER INFORMATION: n = A,T,C or G

<400> SEQUENCE: 1
ccnaaratht tyathaayyt ngcnaaraar aararcgcng gc                          42

<210> SEQ ID NO 2
<211> LENGTH: 42
<212> TYPE: DNA
<213> ORGANISM: Artificial Sequence
<220> FEATURE:
<223> OTHER INFORMATION: Synthetically generated oligonucleotides

<400> SEQUENCE: 2
ccgaaaatat tcatcaacct ggctaagaag aagaaagctg gc                          42

<210> SEQ ID NO 3
<211> LENGTH: 45
<212> TYPE: DNA
<213> ORGANISM: Artificial Sequence
<220> FEATURE:
<223> OTHER INFORMATION: Synthetically generated oligonucleotides
<220> FEATURE:
<221> NAME/KEY: misc_feature
<222> LOCATION: (1)...(45)
<223> OTHER INFORMATION: n = A,T,C or G

<400> SEQUENCE: 3
tsngayggng cngtncarcc ngayggnggn carccngcng tnmgn                       45
```

-continued

<210> SEQ ID NO 4
<211> LENGTH: 45
<212> TYPE: DNA
<213> ORGANISM: Artificial Sequence
<220> FEATURE:
<223> OTHER INFORMATION: Synthetically generated oligonucleotides

<400> SEQUENCE: 4
tcagacggtg ctgtacagcc agatggagga caacccgcgg ttcgc                45

<210> SEQ ID NO 5
<211> LENGTH: 20
<212> TYPE: DNA
<213> ORGANISM: Artificial Sequence
<220> FEATURE:
<223> OTHER INFORMATION: Synthetically generated oligonucleotides

<400> SEQUENCE: 5
tccatgacgt tcctgatgct                                            20

<210> SEQ ID NO 6
<211> LENGTH: 48
<212> TYPE: DNA
<213> ORGANISM: Artificial Sequence
<220> FEATURE:
<223> OTHER INFORMATION: Synthetically generated oligonucleotides

<400> SEQUENCE: 6
aattccccga aaatattcat caacctggct aagaagaaga aagctggc              48

<210> SEQ ID NO 7
<211> LENGTH: 48
<212> TYPE: DNA
<213> ORGANISM: Artificial Sequence
<220> FEATURE:
<223> OTHER INFORMATION: Synthetically generated oligonucleotides

<400> SEQUENCE: 7
tcgagccagc tttcttcttc ttagccaggt tgatgaatat tttcgggg              48

<210> SEQ ID NO 8
<211> LENGTH: 14
<212> TYPE: PRT
<213> ORGANISM: Canine parvovirus
<220> FEATURE:
<223> OTHER INFORMATION: Synthetically generated oligonucleotides

<400> SEQUENCE: 8

Pro Lys Ile Phe Ile Asn Leu Ala Lys Lys Lys Lys Ala Gly
 1 5 10

<210> SEQ ID NO 9
<211> LENGTH: 48
<212> TYPE: DNA
<213> ORGANISM: Artificial Sequence
<220> FEATURE:
<223> OTHER INFORMATION: Synthetically generated oligonucleotides

<400> SEQUENCE: 9
aattcagacg gtgctgtaca gccagatgga ggacaacccg cggttcgc 48

<210> SEQ ID NO 10
<211> LENGTH: 48
<212> TYPE: DNA
<213> ORGANISM: Artificial Sequence
<220> FEATURE:

-continued

```
<223> OTHER INFORMATION: Synthetically generated oligonucleotides

<400> SEQUENCE: 10
tcgagcgaac cgcgggttgt cctccatctg gctgtacagc accgtctg              48

<210> SEQ ID NO 11
<211> LENGTH: 15
<212> TYPE: PRT
<213> ORGANISM: Canine parvovirus
<220> FEATURE:
<223> OTHER INFORMATION: Synthetically generated oligonucleotides

<400> SEQUENCE: 11

Ser Asp Gly Ala Val Gln Pro Asp Gly Gly Gln Pro Ala Val Arg
  1               5                  10                  15

<210> SEQ ID NO 12
<211> LENGTH: 29
<212> TYPE: DNA
<213> ORGANISM: Artificial Sequence
<220> FEATURE:
<223> OTHER INFORMATION: Synthetically generated oligonucleotides

<400> SEQUENCE: 12
cgggatccga gacgacttgg attaaggta                                   29

<210> SEQ ID NO 13
<211> LENGTH: 29
<212> TYPE: DNA
<213> ORGANISM: Artificial Sequence
<220> FEATURE:
<223> OTHER INFORMATION: Synthetically generated oligonucleotides

<400> SEQUENCE: 13
gtgcggccgc tagttgatat gtaataaac                                   29

<210> SEQ ID NO 14
<211> LENGTH: 20
<212> TYPE: DNA
<213> ORGANISM: Artificial Sequence
<220> FEATURE:
<223> OTHER INFORMATION: Synthetically generated oligonucleotides

<400> SEQUENCE: 14
tccatgacgt tcctgatgct                                             20
```

NUCLEIC ACID VACCINATION FOR PARVOVIRAL INFECTIONS

This application claims priority from international patent application no. PCT/EP97/01943, filed Apr. 18, 1997, which is based on German patent application no. 96 10 6217. 1, filed Apr. 19, 1996.

The general field of the invention is a method for nucleic acid vaccination of animals to protect them from parvoviral infections. This invention is more particularly related to the preparation and use of parvoviral DNA and its administration to dogs, cats and mink so as to induce an immune response that can protect these animals from disease caused by virulent parvovirus. Nucleic acid immunogens are designed to include the antigenic portions of the parvoviral genome which are incorporated into bacterial plasmids. These plasmids produce the desired parvoviral gene product when introduced into host cells by transfection. Host cells transfected with the parvoviral immunogen expressing plasmids produce a stream of antigenic proteins to which the host immune system will mount a protective immune response.

Parvoviruses are a family of closely related small DNA viruses composed of a protein capsid containing single stranded DNA. Parvoviruses cause various diseases in a variety of mammalian species. Feline panleukopenia virus, mink enteritis virus and canine parvovirus are host range variants of the feline parvovirus subgroup and share more than 98% DNA homology (Martyn et at, J. Gen. Virol. 71 (1990) 2747–2753). Canine parvovirus is a relatively new pathogen of all canids, having been first recognized in the late 1970's as the causative agent of a world wide pandemic of highly fatal gastroenteritis. This virus is theorized to be a host range mutant of feline parvovirus. When nucleotide sequences of feline and canine parvoviruses were compared, 31 base changes were identified resulting in changes in just 9 amino acids (Martyn et. at., 1990). Six of these amino acid changes were in the major capsid genes VP1 and VP2. The canine specific antigenic epitope is determined by a single amino acid difference from feline panleukopenia virus. Further genetic mapping has recently confirmed the time of origin of canine parvovirus, reinforced the theory of its origin from feline parvovirus, and indicated a continued evolution of the virus in the field strains now being isolated (Truyen et. al., J. of Virology 69 (8) (1995), 4702-4710).

The two nucleocapsid proteins, VP1 and VP2 are expressed from the same RNA with VP2 resulting from an in-frame ATG codon within the VP1 open reading frame. VP2 is expressed at levels nearly 10 fold higher than VP1 indicating that the internal start codon is more efficiently recognized as such by the translational apparatus (Turiso et. al., J. of Gen. Virol. 72 (1991), 2445–2456). Epitope mapping experiments have demonstrated that all of the antigenic epitopes generating neutralizing antibody lie within VP2 (Turiso et. al., 1991, loc. cit.). These include the first 16 amino acids of VP2 (Langeveld et., J. of Virology 68(7) (1994), 4506–4513; Casal et. al., J. of Virology 69 (11) (1995), 7274-7277).

Immunization remains the primary mechanism by which humans and animal species are protected against the scourge of infectious disease. The recent trend in vaccine design away from live, attenuated, agents due to safety concerns, either due to "vaccine breaks", incomplete attenuation, reversion, or amplification in immunosuppressed patients, has also seen an accompanying decrease in vaccine duration and efficacy. The use of killed agents, cloned recombinant proteins or peptides requires large dosages and the presence of adjuvants. However, the long term effects of such adjuvants have not been explored, and they have recently been implicated as causative agents in vaccine induced sarcomas of cats (Hendrick et. al., J. Am. Vet. Med. Assoc. 205 (1994), 1425-1429). Additionally, the extracellular location of the injected antigen raises questions about the way in which those antigens are presented to the immune system, and their appropriateness to generate protection against naturally occurring infections.

Current immunization practices for canine parvovirus are marginal (Schultz, R.D. (1994), The Challenge of Controlling a Newly Recognized Disease: Canine Parvovirus Vaccines, IBC International Symposium, Oct. 27–28, 108). Vaccines consisting of either attenuated or killed organisms, must be given repeatedly to create immunity, and immunization in the face of circulating maternal antibody titers does not usually occur. This problem is compounded by the ability of maternal antibody to inactivate vaccine while having been reduced to levels that are not protective leading to a "window of vulnerability" (Pollock and Carmichael, J. Am. Vet. Med. Assoc. 130 (1982), 3742). The cloning of canine parvovirus has led to the development of two distinct vaccine strategies. The first was the introduction of the entire VP2 sequence into a baculovirus expression system. The protein product was harvested, and used to successfully immunize dogs (Turiso et. al., J. of Virology 66 (5) (1992), 2748–2753). The second strategy involves the subcloning or synthesis of peptide epitopes which are used to immunize dogs. These peptides have utilized the amino terminus sequence of VP2 (Casal et. al., 1995, loc. cit.) which resulted in successful immunization of dogs. The vaccines developed using these strategies have also been tested with mink enteritis virus, another closely related host range variant of parvovirus. Administration of either recombinant protein or peptide results in protective immunity to this commercially relevant disease of mink (Langeveld et. al., Vaccine 13(11) (1995),1033–1037).

Modified live virus vaccines for feline panleukopenia are effective in protecting adult cats, but may produce birth defects in kitten embryos in utero, consequently they are not recommended for vaccinating intact female cats which could be pregnant. Because of the serious limitations of modified live virus vaccines, investigators began to explore the possibility of transfecting cells in vivo with genes expressing antigens from infectious organisms (reviewed in Donnelly et. al., J. lmm. Meth. 176 (1994), 145152; Fynan et. al., Int. J. Immunopharmac. 17 (2) (1995), 79–83; Whalen et. al. (1995), DNA Mediated Immunization to the Hepatitis B Surface Antigen; Activation and Entrainment of the Immune Response in DNA Vaccines, New York: New York Academy of Sciences). Such a mechanism of immunization would imitate the pathway of viral gene expression without the attendant risk posed by attenuated organisms, while bypassing the need for typical adjuvants. The serendipitous discovery that intramuscular injection of "naked" plasmid DNA carrying a mammalian promoter would cause the DNA to be taken up by muscle cells and expressed (Wolff et. al., Science 247 (1990) 1465–1468), has led to a dramatic expansion of the new field of nucleic acid vaccination. Subsequent to the original study, conditions affecting intramuscular injection of plasmid DNA have been further defined and broadened (Wolff et. al., Biotechniques 11 (1991), 474–485). The efficiency of transfer is relatively low, ranging from 1–5%, however that efficiency can be increased up to 40 fold by inducing muscle degeneration prior to the injection of plasmid DNA (Vitadello et. al., Hum. Gene. Ther. 5 (1994), 11–18; Danko and Wolff, Vaccine 12

(16) (1994), 1499–1502); Davis et. al., Hum. Gene. Ther. 4 (1993), 733–740). Two of the most commonly used myo-necrotic agents are the local anesthetic bupivicaine, and cardiotoxin (Danko and Wolff, 1994, loc. cit.; Davis et. al., 1993, loc. cit.). A number of other techniques have been employed to transfer genes to muscle including retroviral vectors, adenoviral vectors, and liposomes. However, direct injection of naked DNA appears to be the most efficient of these delivery mechanisms at transferring and expressing foreign DNA (Davis et. al., 1993, loc. cit.).

Several routes of administration have been explored in addition to intramuscular injection. Common to all of these routes is the lack of a need for any agent or vector to facilitate the entry of the nucleic acid into target cells. Intravenous, intraperitoneal, intradermal, intranasal and subcutaneous injection of DNA plasmids have all resulted in immunization against influenza virus hemagglutinin (HA) in chickens (reviewed in Pardoll and Beckerkleg, Immunity 3 (1995), 165–169). Interestingly, these studies indicated that mucosal (intranasal) immunization with DNA did not produce the expected IgA response, but rather an IgG response, as seen with intramuscular injections. Additionally, intradermal immunization by bombardment with DNA coated gold microparticles was shown to be as efficacious as other methods of gene delivery at 100 to 1000 fold lower DNA concentrations than the other methods. Similar experments have demonstrated that the intradermal, and intravenous routes result in immunization in mice and rabbits (Raz et. al., Proc. Natl. Acad. Sci. USA 91 (1994), 9519–9523). Emphasizing the simplicity of the approach, Raz and colleagues have indicated that there is the potential of bypassing the expensive and potentially cumbersome equipment required for tissue bombardment and intradermal immunization by coating a plastic tuberculin PPD tine with DNA and scarifying the skin to achieve similar result to biolistic bombardment. DNA immunization has been tried with varying success in several mammalian species including cattle, swine, and non-human primates, predominantly by the intramuscular route.

The nature of the immune response to antigens present after intramuscular injection of DNA expression constructs has been reported to involve both the humoral and cellular arms of the immune system. When reporter DNA constructs are injected, they appear to be contained within mature myofibers. This is supported by the evidence that muscle regeneration appears to increase the efficiency of plasmid expression. Antigen presentation might occur by MHC class I presentation by the muscle cell, antigen uptake from myocytes by bone marrow derived antigen presenting cells (APCs) or by direct DNA transfection of APCs that are migrating through muscle (reviewed in Pardoll and Beckerleg, 1995, loc. cit.; Whalen et. al., 1995, loc. cit.). Simple antigen presentation by myocytes would seem unlike to be completely responsible for this phenomenon for two reasons. First is the growing body of evidence that presentation of antigen in the absence of co-stimulatory signals such as B7 and B7-2 results in tolerization to antigens (Chen and Nabavi, Immunity 1 (1994), 147–154). Secondly, muscle has been reported to have extremely low levels of expression of MHC class I (Karpati et. al., Ann. Neurol. 23 (1988), 64–72). Therefore, it seems likely that antigen presentation is performed by professional APCs that have acquired antigen either by scavenging it or through direct acquisition and expression of the transferred gene (Pardoll and Beckerleg, 1995, loc. cit.; Whalen et. al., 1995, loc. cit.). An experiment performed with biolistic particle bombardment in the mouse would seem to favor the latter approach.

Mice were bombarded in the pinna and the ear surgically removed five minutes after bombardment. These mice retained the ability to form an immune response, and that response did not differ qualitatively from that induced by bombardment alone. Clearly, a highly mobile cell population must be responsible for initiating and maintaining the immune response in these mice. The dendritic cell has been proposed as this cell (Fynan et. al., 1995, loc. cit.). Significantly, the character of the immune response induced by particle bombardment differs slightly from the response resulting from intramuscular injection, with IgG1 predominating in intramuscular injections while IgG2 predominates in intradermal injections. The primary reason for this difference may rest in the myocytes, which in intramuscular immunization, continue to express antigen for periods exceeding one month (Pardoll and Beckerleg, 1995, loc. cit.). This continuous expression results in what has been called immune entrainment (Whalen et. al., 1995, loc. cit.). The practical result of this phenomenon is that muscle expression acts as a continuous boost. Frequently, titers from a single injection may rise over a period of 4 to 8, or even more weeks. Classic booster responses have also been observed with injections of DNA given over 6 months after the primary injection. Curiously, DNA booster injections, given during the period of rising antibody titers, may have no effect, or may even reduce the response to antigen (Davis et al., "Introduction of systemic and mucosal immunity to HBV with plasmid DNA", International Meeting on Nucleic Acid Vaccines, Feb. 5–7, 1996, Bethesda, Md. USA).

The ability to generate a measurable immune response is not a priori sufficient for vaccination. Rather the immune response must contain the appropriate elements to protect the host from infection, invasion, and disease. Therefore, protection against infection in challenge studies remains the single most convincing demonstration of vaccine efficacy. DNA based vaccines have been able to protect chickens against lethal influenza virus challenges (Robinson et. al., Vaccine 9 (1993), 957–960) and mice against *Mycoplasma pulmonis* infection (Lai et. al., DNA and Cell Biology 14(7) (1995), 643–651). Additionally, mice could be protected against the establishment of persistent infections of lymphocytic choriomeningitis virus by DNA immunization (Martins et. al., J. of Virology 69(4) (1995), 2574–2582).

The prior art, with respect to nucleic acid vaccination as related to the present invention is summarized in the following articles: Donnely et al, 1994, loc. cit., Fynan et al., 1995, loc. cit., Whalen et al., 1995, loc. cit. as regards nucleic acid vaccination, and Turiso et al., 1992, loc. cit. and Casal et al., 1995, loc. cit., as regards parvoviral vaccination.

The above recited prior art only tested the immune response of mice to vaccination with nucleic acids. As is well known in the art, experimental results obtained with mice cannot be transferred to animals like cats, dogs and mink due to the taxonomic difference between these animals. Since, on the other hand, no suitable vaccines against parvoviral infections of canids, felids and mustelids could be provided by the prior art, the technical problem underlying the present invention was to provide such a vaccine. Said vaccine should effectively protect in particular dogs, cats and mink from the potentially life threatening effect of parvovirus infections. The solution to the above technical problem is achieved by providing the embodiments characterized in the claims.

Accordingly, the present invention relates to an anti-parvovirus vaccine comprising nucleic acid molecules encoding at least one parvovirus-specific epitope and a pharmaceutically acceptable carrier. Surprisingly, in accordance with the invention it has now been found that immunization with "naked" DNA that encodes at least one parvovirus-specific epitope yields an immune response that protects the vaccinated animal from parvovirus-induced disease upon subsequent parvoviral infection.

In a preferred embodiment of the anti-parvovirus vaccine of the invention, at least one of said parvovirus-specific epitopes is a T-cell epitope. The person skilled in the art, when designing a protective vaccine in the light of the teachings of the present invention, is able to devise a vaccine comprising a nucleic acid sequence encoding only a T-cell epitope to be used in the vaccine of the invention.

Similarly, the person skilled in the art is able to devise a vaccine comprising only a B-cell epitope encoding DNA for use in a nucleic acid vaccine according to the present invention. Therefore, in a further preferred embodiment, the anti-parvovirus vaccine comprises at least one B-cell epitope. Alternatively, nucleic acids encoding said at least one B-cell epitope can be comprised in said vaccine together with nucleic acids encoding at least one T-cell epitope. T- and B- cell epitopes may be encoded by the same or different DNA molecules.

In a further preferred embodiment of the anti-parvovirus vaccine according to the invention, said nucleic acid molecules are DNA molecules or RNA molecules. The term "DNA molecules" is used here in its broadest sense and includes e.g. cDNA molecules, genomic DNA, synthetic and semisynthetic DNA molecules. Equally, the term "RNA molecules" is used in its broadest possible sense herein.

In a further preferred embodiment of the anti-parvovirus vaccine according to the invention, said nucleic acid molecules encode the parvoviral VP1 and/or VP2 nucleocapsid proteins.

The parvoviral genome is approximate 5000 base pairs long, and contains approximately four open reading frames. Two of these open reading frames encode, VP1 and VP2, the major capsid proteins of parvovirus. VP2 is contained within VP1 and consist of all but a small portion of the 5' end of the VP1 gene or the amino terminus of the VP1 protein. The sequence exclusive to VP1 is known to encode an epitope which is responsible for stimulating a T-cell response. The sequence common to VP1 and VP2 encodes at least one epitope which stimulates an antibody response. Natural infections with parvoviruses generate significant protective responses within one week of infection. Expression of the entire VP1 gene or the epitope within VP1 (and VP2) also results in protective immunity through both the cellular and humoral arms or the immune system.

Accordingly, the person skilled in the art may use nucleic acid sequences comprising either the sequence encoding the VP1 epitope as a representative of a parvoviral T-cell epitope or a nucleic acid sequence encoding the VP2 epitope as a representative of a parvoviral B-cell epitope or a combination of both for the preparation of a vaccine for immunizing canids, felids or mustelids.

In a particularly preferred embodiment of the vaccine of the invention, said nucleic acid molecules comprise the complete VP1 open reading frame, i.e. the reading frame encoding the VP1 nucleocapsid protein. In the case of the canine parvovirus, the complete length of the open reading frame is 2169 base pairs. Said orf is preferably expressed under the control of a suitable foreign promoter.

A further preferred embodiment of the vaccine of the invention, said epitope is derived from a parvovirus-genome, said parvovirus being capable of infecting canids, felids or mustelids and preferably dogs, cats or mink. Due to the strong overall homology of the genome of parvoviruses infecting either canids, felids or mustelids, a vaccine derived from a nucleic acid derived from either canids, felids or mustelids can be used to successfully immunize any of the other groups of animals mentioned.

In an additional preferred embodiment of the vaccine of the present invention, said nucleic acid molecules encoding at least one parvovirus-specific epitope are comprised in an expression vector, said expression vector being functional in mammalian cells.

To the person skilled in the art, numerous suitable expression vectors for carrying out the present invention are available. Accordingly, the vectors recited in the attached examples as a starting basis for developing the vaccine of the present invention are not in any way intended to limit the scope of the present invention. Further suitable vectors are available from commercial companies including Invitrogen, Vical, and Agracetus and can be readily produced by the person skilled in the art.

An additional preferred embodiment of the invention relates to an anti-parvovirus vaccine, wherein said vaccine comprises or said expression vector encodes at least one additional antigen.

Said additional antigen may serve the function to enhance the immune response to the parvovirus-specific epitope. In this regard, said additional antigen has the function of a carrier protein. Alternatively, the different antigen may induce an immune response to a different pathogen and thus serve the function of creating a multivalent vaccine. It is also possible that the additional antigen serves both functions.

There are multiple ways to devise a vector that encodes at least one parvovirus-specific epitope as well as at least one additional antigen. Thus, for example, the nucleic acid encoding the additional antigen may be cloned into the nucleic acid sequence encoding the at least one parvovirus-specific epitope. If no suitable restriction site is located within said nucleic acid sequence encoding said parvovirus-specific epitope, such a restriction site can be generated using conventional methods. Conversely, the nucleic acid sequence encoding said at least one parvovirus-specific epitope may be cloned into a DNA sequence encoding said at least one additional antigen. The resulting polypeptide may be a fusion protein. Alternatively, the at least one parvovirus-specific epitope and the at least one additional antigen may be expressed as separate proteinaceous entities.

It is clear from the statements made in the previous paragraph that a particular preferred embodiment of the invention relates to a vaccine, wherein said additional antigen is an immunogen.

An example of such an immunogen which has turned out to be effective as a carrier molecule, is the hepatitis B-surface antigen, and preferably the human hepatitis B-surface antigen pre-S2 protein.

An additional particularly preferred embodiment of the invention relates to a vaccine comprising the recombinant vector pGT36VP1. Said vector comprises a nucleic acid molecule that represents the complete VP1 open reading frame. The detailed construction of said vector is described in Example 2.

In a further particularly preferred embodiment of the vaccine of the present invention, said nucleic acid molecule encoding at least one T-cell epitope is selected from the group of epitopes encoded by the degenerate nucleic acid sequence C C N A A R A T H T T Y A T H M Y Y T N G C N M - RAARAARAARGCNGGC (SEQ ID NO: 1);

wherein N denotes any base, R denotes purine, Y denotes pyrimidine and H denotes A, C or T;

and is preferably the epitope encoded by the nucleic acid sequence

CCGAAAATA7TCATCAACCTGGCTMGAAGAAGAAAGCTGGC (SEQ ID NO: 2).

In a further particularly preferred embodiment of the vaccine of the present invention, said nucleic acid molecules encoding at least one B-cell epitope is selected from the group of epitopes encoded by the degenerate nucleic acid sequence

TSNGAYGGNGCNGTNCARCCNGAYGGNG-GNCARCCNGCNGTNMGN (SEQ ID NO 3);

wherein N denotes any base, R denotes purine, Y denotes pyrimidine, S denotes G or C and M denotes C or A; and is preferably the epitope encoded by the nucleic acid sequence

TCAGACGGTGCTGTACAGCCAGATGGAG-GACAACCCGCGGTTCGC (SEQ ID NO: 4).

In an additional preferred embodiment, the vaccine of the present invention comprises a mixture of nucleic acids encoding both T-cell and B-cell epitopes.

An example of this embodiment of the invention is the case that any of the previously mentioned nucleic acid molecules encoding said at least one B- and T-cell epitopes are comprised in different expression vectors.

In a further preferred embodiment of the anti-parvovirus vaccine of the invention, said vaccine additionally comprises an adjuvant.

Adjuvants for immunization are well known in the art and suitable adjuvants can be combined with the nucleic acid sequences described in the previously mentioned embodiments for the formulation of a vaccine by the person skilled in the art.

A particularly preferred embodiment of the present invention relates to a vaccine, wherein said adjuvant is a DNA molecule comprising unmethylated CpG motifs. DNA has long been known to contain the genetic information that makes each individual unique. In addition to this role as blueprint of the cell, Dr. Arthur Krieg has recently discovered a short stretch of DNA, called a CpG motif, that causes potent immune activation (Nature (1995), Vol 374, 546). DNA with CpG motifs ("CpG DNA") can be synthesized easily and inexpensively, and used to selectively activate the immune system. Therapeutic applications for CpG DNA-mediated immune activation include increasing the effectiveness of vaccines, helping the immune system to destroy cancer, and preventing or treating infection. DNA is a natural part of the body, and may be much safer than drugs now used toe enhance the immune system; see patent application U.S. Ser. No. 08/386,063; now U.S Pat. No. 08/461,036; 6/184,388 08/462,799 now abandoned This invention combines for the first time the use of plasmid DNA as a vaccine together with CpG containing oligonucleotides functioning as adjuvant for the DNA based vaccine.

The superior immunological properties of this vaccine is described in the attached examples.

Particularly preferred is an anti-parvovirus vaccine, wherein said DNA molecule comprising unmethylated CpG motifs is

TCCATGACG7TCCTGATGCT (SEQ ID NO5).

In a further particularly preferred embodiment of the anti-parvovirus vaccine of the invention, said DNA molecule comprising unmethylated CpG motifs comprised a phosphorothioate-modified backbone.

The phosphorothioate modification is particularly advantageous since it appears to further enhance the adjuvant capacities of the unmethylated CpG motifs; see, e.g. Krleg et al., loc. cit.

With the vaccine according to the present invention it is possible to obtain an effective immunization even if the vaccine is only applied once.

Additionally, the present invention relates to the use of an anti-parvovirus vaccine of the invention for the vaccination of canids, felids or mustelids, a method for vaccinating canids, felids or mustelids by administering a suitable dose of the vaccine of the invention to an animal in need thereof, as well as to the use of the ingredients of the vaccine of the invention mentioned hereinabove, such as nucleic acids specified in the various embodiments or adjuvants, such as the unmethylated CpG motifs, or any combination thereof for the preparation of a vaccine for the immunization of canids, felids or mustelids against parvoviral disease.

Preferably, said canids, felids or mustelids are dogs, cats or mink. The person skilled in the art, here, a veterinarian, is perfectly aware of which dose and application route should be applied. Additionally he is familiar with the number of vaccine applications as well as the optimal time span between primary and booster vaccinations.

In a particularly preferred embodiment the vaccine according to the invention is used for a vaccination protocol in which the vaccine is only applied once and leads to a sufficient immunization ("single dose immunization").

The vaccine of the invention is preferably administered by one of the following routes: intramuscular by needle and syringe, intramuscular by Biojector 2000®, intradermal by needle and syringe, intradermal by particle bombardment, intradermal by scarification, intravenous or intraperitoneal. The examples illustrate the invention.

EXAMPLE 1

SYNTHESIS OF ANTIGENIC EPITOPES OF THE FELINE PARVOVIRUS SUBGROUP

Synthetic deoxyribonucleic oligonucleotides were produced with the sequence

AATTCCCCGAAAATATTCATCAACCTGGCTAAGAAGMGAAAGCTGGC (SEQ ID NO: 6) and the complementary strand

TCGAGCCAGCTTTCTTCTTCTTAGCCAGGTTGATGAATATTTTCGGGG (SEQ ID NO: 7)

which when annealed to each other contain overhangs which will bind to an Eco RI and Xho I restriction site, and in the proper reading frame, encode the T-cell epitope of VP1, PKIFINLAKKKKAd (SEQ ID NO: 8). These oligonucleotides were ligated into the Eco RI and Xho I sites in the pre S2 region of Human Hepatitis B. Surface antigen in the plasmid pCMV-S2S (Michel et al., Proc. Natl. Acad. Sci. USA 92 (1995), 5307–5311) in the process deleting the majority of the pre S2 region. The resulting construct was termed pCMVS-VP1e. The RNA transcript produced from the CMV promoter in this construct contains an open reading frame with an internal start codon (AUG). When the first ATG is used, the VP1 epitope, part of the pre S2 region and all of the S region are produced as a single protein. The internal AUG produces only the S protein. Similarly, deoxyribonucleic oligonucleotides with the sequence AATTCAGACGGTGCTGTACAGCCAGATGGAGGACAACCCGCGGTTCGC (SEQ ID NO: 9) and the complementary strand

TCGAGCGAACCGCGGGTTGTCCTCCATCTGGCTGTACAGCACCGTCTG (SEQ ID NO: 10)

which encode the peptide epitope SDGAVQPDGGQPAVR (SEQ ID NO: 11), from VP2, were cloned into pCMV-S2S in the same manner as the VP1 epitope, The resulting plasmid was named pCMVS-VP2e. Both of the DNA sequences encoding these epitopes are artificial sequences, and do not represent the DNA sequence from naturally occurring parvoviruses.

EXAMPLE 2

CLONING THE VP1-VP2 GENE OF CANINE PARVOVIRUS AND CONSTRUCTION OF PLASMIDS EXPRESSING PARVOVIRUS GENES

The entire coding region of canine parvoviral VP1 (VP1 and VP2) was cloned by polymerase chain reaction amplification from tissue culture supernatants containing CPV type 2a. The primers were located just outside the open reading frame for VP1, included Not I (downstream) and BamH I (upstream) restriction sites and had the following sequences:

cgg gat ccG AGA CGA CTT GGA TTA AGG TA (SEQ ID NO: 12), for the 5' or upstream primer, and gtg cgg ccg CTA GTT GAT ATG TM TAA AC (SEQ ID NO: 13), for the 3' or downstream primer.

The PCR product was sequentially restricted with Not I and BamH I and ligated into similarly digested bacterial expression plasmid pGT36 (Conry et al, Cancer Gene Therapy 2(1) (1995), 33–38 in the sense orientation. Orientation and sequence of VP1 (and VP2) were confirmed by DNA sequencing of the entire VP1 insert. This DNA cloned will be referred to as pGT36VP1.

EXAMPLE 3

EXPRESSION OF THE CLONED PARVOVIRUS VP1-VP2 GENE IN CULTURED CELLS

A murine fibroblast (NIH 3T3) was transfected with the pGT36VP1 clone. Cells were then examined for the presence of immunoreactive canine parvoviral proteins by immunofluorescent assay with a canine antiserum to canine parvovirus. The pattern of staining was indistinguishable to cells infected with canine parvovirus, while negative controls (pGT36, no DNA) showed no staining, indicating that the pGT36VP1 clone produced a protein product recognized by anti-parvoviral antibodies.

EXAMPLE 4

IMMUNIZATION OF DOGS WITH PARVOVIRUS (EPITOPE) NUCLEIC ACID VACCINES

Three 11 week old puppies were immunized with 150 μg pCMVS-VP1 e and 100 μof the synthetic phosphorothioate oligonucleotide TCCATGACGTTCCTGATGCT (SEQ ID NO: 14), (ISO) in the right quadricepts muscle, three 11 week old puppies were immunized with 150 μg pCMVS-VP2e and 100 μg of the ISO, and three 11 week old puppies were immunized with 150 μg PCMVS-VP1e, 150 μg pCMVS-VP2e, and 100 μg of the ISO. The puppies were boosted 3 weeks later with identical doses, and monitored for the development of antibody titers to the carrier protein, Hepatitis B surface antigen, and the canine parvoviral epitopes. A significant antibody response was seen to both hepatitis and canine parvovirus in the animals in the pCMVS-VP1e plus pCMVS-VP2e, and the pCMVS-VP2e groups. No antibody response was expected to canine parvovirus in the pCMVS-VP1e as this represents a T-cell epitope. This expectation was confirmed experimentally. The response was greatest in the pCMVS-VP1e plus pCMVS-VP2e indicating that the multivalent vaccine was more effective.

EXAMPLE 5

IMMUNIZATION OF ANIMALS WITH A NUCLEIC ACID EXPRESSING PARVOVIRUS VP1 AND VP2 GENES (a) One of three Balb-c mice immunized with pGT36VP1 demonstrated an immune, in particular an antibody response to canine parvovirus one week after particle bombardment with 1 μg of the plasmid.

(b) Three juvenile (approximate age 6 months) beagle dogs with no anti-canine parvovirus antibody titers were immunized with 150 μg of pGT36VP1 and 100 μg of the ISO in the right quadriceps muscle. Significant anti-canine parvovirus antibody responses developed beginning within 2 weeks of immunization in one animal, and continuing to increase for at least 3 weeks in all three animals. A control beagle, injected with the vector DNA and ISO showed no increase in antibody titer.

(c) Six juvenile dogs with no anti-canine parvovirus antibody titers were immunized with 400μg of pGT36VP1 in the right quadriceps muscle. Three of these dogs received an additional 400μg of DNA from E. coli as an immunostimulatory adjuvant, which was coadministered with pGT36VP1. All six dogs showed anti-parvovirus antibody response within two weeks of immunization, which reached titers significantly above that known to be protective in 3 to 5 weeks. The three dogs receiving immunostimulatory DNA reached higher antibody titers, more rapidly than the other dogs, indicating a positive CpG immune stimulatory effect.

EXAMPLE 6

PROTECTION OF DOGS, IMMUNIZED WITH A NUCLEIC ACID VACCINE EXPRESSING PARVOVIRUS VP1 AND VP2 GENES, FROM CHALLENGE INFECTION OF CANINE PARVOVIRUS (a) The three beagle dogs immunized in example 5 were challenged with a standard tri-valent dose of canine parvovirus, used in parvoviral vaccine trials, via the intranasal route. None of the dogs showed any signs of parvoviral related illness indicating protection from disease. Two dogs shows slight increase in anti-canine parvovirus antibody responses, consistent with the pre-challenge trend, with no fecal shedding of parvovirus, indicating complete protection from infection. The control beagle showed signs of parvoviral disease following challenge, accompanied by a dramatic increase of anti-canine parvovirus antibody response.

(b) Four juvenile dogs with no anti-canine parvovirus antibody titers were immunized intramuscularly with doses of pGT36VP1 including 200, 400, 600, and 800μg of plasmid. All dogs developed anti-canine parvovirus antibodies within one week, which peaked to protective titers within 2 weeks. A negative control dog injected with saline showed no anti-canine parvovirus antibody. The dog receiving 600μg of plasmid DNA sustained an antibody titer longer than the other dogs. All dogs were reinjected 16 weeks after the initial injection with the same preparation and dose. All dogs except the negative control and 200μg dose showed an anamnestic antibody response. All dogs except the negative control, but including the 200μg dose showed serum neutralizing antibody titers after reinjection known to be protective. All dogs were challenged at 24 weeks after initial injection with virulent street virus containing three virus isolates known to cause disease in unimmunized dogs. All dogs immunized with pGT36VP1 nucleic acid vaccine were protected from infection and disease. The negative control dog had clinical disease typical of canine parvovirus and shedded virus in the stool. This experiment demonstrates that doses of pGT36VP1 ranging from 200 to 800μg of plasmid, given as a primary and booster injection stimulated production of antibody titers and protected against virulent challenge.

(c) Three juvenile dogs with no anti-canine parvovirus antibody titers were injected with 150μg of pGT36VP1 plus 150μg of oligonucleotide DNA synthesized to contain optimal CpGs. All dogs developed anti-canine parvovirus antibody and were protected from challenge with virulent virus. This experiment demonstrates that immunization with a lower dose of pGT36VP1 will confer protective immunity when immunization is amplified with immunostimulatory oligonucleotides.

(d) Six juvenile dogs with no anti-canine parvovirus antibody titers were injected with a single dose of 200 or 800μg of pGT36VP1. All dogs developed anti-canine parvovirus antibody titers initially, which decayed to undetectable levels by 12 weeks post immunization. Without giving a booster immunization, all dogs were challenged with virulent virus and none became infected or ill. This experiment demonstrates that protective immunity is achieved after a single dose of pGT36VP1 and this protection is independent of the presence of measurable anti-canine parvovirus antibody. This result can be interpreted as resulting from cellular immunity conferred by long lived immunological memory T-cells.

These studies demonstrate that selected DNA sequences from the feline parvovirus subgroup when inserted into a mammalian expression plasmid can transfect cells in culture and in animals. Furthermore, it was demonstrated that our DNA expression plasmids can invoke an antibody response in animals which may lead to protection against virulent viral challenge.

What is claimed is:

1. An anti-parvoviral vaccine comprising:

a) a vector comprising a nucleic acid sequence encoding at least one polypeptide selected from the group consisting of:
   i) VP1;
   ii) VP2; and
   iii) the N-terminal 23 residues of VP2 or an immunogenic fragment thereof;

b) an adjuvant; and c) a pharmaceutically acceptable carrier.

2. The anti-parvovirus vaccine according to claim 1, wherein said adjuvant is a DNA molecule comprising unmethylated CpG motifs.

3. The anti-parvovirus vaccine according to claim 2, wherein said DNA molecule comprising unmethylated CpG motifs is TCCATGACGTTCCTGATGCT (SEQ ID NO:5).

4. The anti-parvovirus vaccine according to claim 2 or 3, wherein said DNA molecule comprises a phosphorothioate-modified backbone.

5. The anti-parvoviral vaccine according to claim 1, wherein said vector is designated pGT36VP1.

6. The anti-parvoviral vaccine of claim 1, wherein the polypeptide is the amino acid sequence of SEQ ID NO:11.

7. A method of eliciting an immune response capable of preventing parvoviral infection in a subject comprising administering to the subject an anti-parvoviral vaccine comprising:

a) a vector comprising a nucleic acid sequence encoding at least one polypeptide selected from the group consisting of:
   i) VP1;
   ii) VP2; and
   iii) the N-terminal 23 residues of VP2 or an immunogenic fragment thereof, and b) a pharmaceutically acceptable carrier, wherein said administration elicits an immune response capable of preventing parvoviral infection in said subject.

8. The method according to claim 7, wherein said immune response is generated by a single administration of the vaccine.

9. The method according to claim 7, wherein the subject is a canid, a felid or a mustelid.

10. The method according to claim 9, wherein the canid, felid or mustelid is a dog, cat or mink, respectively.

11. The method according to claim 7, wherein said vaccine is administered intramuscularly, intradermally, intravenously or intraperintoneally.

12. The method according to claim 7, wherein the vaccine further comprises an adjuvant.

13. The method according to claim 12, wherein the adjuvant is a DNA molecule comprising unmethylated CpG motifs.

14. The method according to claim 13, wherein the unmethylated CpG motifs are TCCATGACGTTCCTGATGCT (SEQ ID NO:5).

15. The method according to claim 13, wherein the DNA molecule comprises a phosphorothioate-modified backbone.

16. The method of claim 7, wherein the polypeptide is the amino acid sequence of SEQ ID NO:11.

17. A pharmaceutical composition comprising:

a) a vector comprising a nucleic acid sequence encoding at least one polypeptide selected from the group consisting of:

i) VP1;

ii) VP2; and iii) the N-terminal 23 residues of VP2 or an immunogenic fragment thereof;

b) an adjuvant; and c) a pharmaceutically acceptable carrier.

18. The pharmaceutical composition of claim 17, wherein the polypeptide is the amino acid sequence of SEQ ID NO:11.

* * * * *